(12) United States Patent
Farhadi

(10) Patent No.: US 9,521,945 B2
(45) Date of Patent: Dec. 20, 2016

(54) ENDOSCOPE ACCESSORY

(71) Applicant: Ashkan Farhadi, Irvine, CA (US)

(72) Inventor: Ashkan Farhadi, Irvine, CA (US)

( * ) Notice: Subject to any disclaimer, the term of this patent is extended or adjusted under 35 U.S.C. 154(b) by 240 days.

(21) Appl. No.: 13/900,524

(22) Filed: May 22, 2013

(65) Prior Publication Data
US 2013/0281781 A1 Oct. 24, 2013

Related U.S. Application Data

(63) Continuation-in-part of application No. 12/266,953, filed on Nov. 7, 2008.

(51) Int. Cl.
| | | |
|---|---|---|
| A61B 1/04 | (2006.01) |
| A61B 1/00 | (2006.01) |
| A61B 1/273 | (2006.01) |
| A61B 8/12 | (2006.01) |
| A61B 1/015 | (2006.01) |
| A61B 1/012 | (2006.01) |
| A61B 1/018 | (2006.01) |
| A61B 8/00 | (2006.01) |
| A61M 25/06 | (2006.01) |
| A61B 1/005 | (2006.01) |
| A61M 25/10 | (2013.01) |

(52) U.S. Cl.
CPC ....... *A61B 1/00135* (2013.01); *A61B 1/00082* (2013.01); *A61B 1/00094* (2013.01); *A61B 1/00137* (2013.01); *A61B 1/00147* (2013.01); *A61B 1/00154* (2013.01); *A61B 1/015* (2013.01); *A61B 1/018* (2013.01); *A61B 1/0125* (2013.01); *A61B 1/2736* (2013.01); *A61B 8/12* (2013.01); *A61B 8/445* (2013.01); *A61M 25/0662* (2013.01); *A61B 1/005* (2013.01); *A61M 25/1011* (2013.01); *A61M 2025/1052* (2013.01)

(58) Field of Classification Search
USPC .......................... 600/114–115, 120–125, 194
See application file for complete search history.

(56) References Cited

U.S. PATENT DOCUMENTS

| | | | | |
|---|---|---|---|---|
| 4,453,545 | A | * | 6/1984 | Inoue ........................ 128/207.15 |
| 5,217,001 | A | * | 6/1993 | Nakao et al. ................. 600/123 |
| 5,499,625 | A | * | 3/1996 | Frass et al. ............. 128/207.15 |
| 5,660,175 | A | * | 8/1997 | Dayal ..................... 128/207.15 |
| 5,762,604 | A | * | 6/1998 | Kieturakis ........ A61B 17/00008 600/104 |
| 5,855,569 | A | * | 1/1999 | Komi ........................... 604/526 |
| 6,126,635 | A | * | 10/2000 | Simpson ........ A61B 17/320758 604/101.05 |

(Continued)

*Primary Examiner* — Matthew J Kasztejna

(57) ABSTRACT

This invention relates generally to an endoscope accessory. This device uses an overtube with an inflatable positioning ring that can be inflated after placement of the overtube just proximal to the tip of the endoscope or echoendoscope. A catheter with an occlusion balloon at its free endportion is carried by the overtube and extends beyond the tip of the endoscope, distal to the part of the body cavity that needs to be examined. Inflation of this balloon together with positioning ring creates a closed space within the body cavity that can be filled with air or water for improving the quality of the examination with regular endoscope of echoendoscope, respectively, while reducing the examination complications.

15 Claims, 8 Drawing Sheets

(56) References Cited

U.S. PATENT DOCUMENTS

| | | | |
|---|---|---|---|
| 6,355,013 B1* | 3/2002 | van Muiden | A61M 25/10 604/164.05 |
| 6,440,061 B1* | 8/2002 | Wenner et al. | 600/114 |
| 6,461,294 B1* | 10/2002 | Oneda et al. | 600/116 |
| 6,550,475 B1* | 4/2003 | Oldfield | 128/200.26 |
| 6,569,085 B2* | 5/2003 | Kortenbach et al. | 600/104 |
| 7,052,456 B2* | 5/2006 | Simon | 600/120 |
| 8,430,809 B2* | 4/2013 | Cabiri | A61B 1/00082 600/114 |
| 8,863,746 B2* | 10/2014 | Totz | 128/207.15 |
| 8,998,798 B2* | 4/2015 | Hayman et al. | 600/120 |
| 2004/0199196 A1* | 10/2004 | Ravo | A61B 1/00082 606/194 |
| 2005/0059931 A1* | 3/2005 | Garrison | A61M 25/10 604/101.04 |
| 2007/0137651 A1* | 6/2007 | Glassenberg et al. | 128/207.15 |
| 2009/0227835 A1* | 9/2009 | Terliuc | A61B 1/00082 600/106 |
| 2013/0281781 A1* | 10/2013 | Farhadi | 600/116 |

\* cited by examiner

ENDOSCOPE ACCESSORY

CROSS-REFERENCE TO RELATED APPLICATION

This application is a continuation-in-part of U.S. Ser. No. 12/266,953 filed on Nov. 7, 2008 and incorporated herein by reference.

FIELD OF INVENTION

This invention relates generally to an accessory for endoscopic examination of body organs particularly gastrointestinal tract. More particularly, the invention relates to creation of a closed region around the tip of an endoscope introduced into a visceral organ.

BACKGROUND OF INVENTION

An endoscope is a well-known optical system for evaluation of internal organs that was disclosed and claimed in U.S. Pat. No. 3,449,037 to C. J. Koester. Currently used fiberoptic endoscopes are comprised of many lenses mounted in a flexible tube to relay an image from inside a body cavity for viewing by a physician for diagnosis or manipulation inside cavitary spaces. Endoscopic ultrasound (EUS) is a device that combines endoscopy and ultrasound to image the gastrointestinal wall and surrounding structures. The first prototype for human use was developed in 1980, and several generations of echoendoscopes have been developed since then. In the 1990 the capability of obtaining tissue samples by this method resulted in further applications of this test to sample internal structures and organs. The ultrasound transducer is positioned at the tip of endoscope and the key components of the transducer are the piezoelectric crystals that vibrate to produce ultrasonic waves. The ultrasonic waves then travel through gastrointestinal lumen to its wall and beyond the visceral wall into the surrounding organs and the reflection of these ultrasound waves will be detected by the same crystals at the transducer and reconstruction of these reflections will result in creating a real time image of the gastrointestinal wall and its surrounding structures. The ultrasonic wave reflects from the surface of structures with different density and can pass very well through fluid containing and solid structures. However, air creates a barrier to ultrasonic wave passage and hampers obtaining ultrasonic images. Thus many attempts have been done to minimize the amount of interfering air between the transducer and the examining structure. These efforts could be seen in early patents by Yokoi in 1988 (Ultrasonic endoscope, U.S. Pat. No. 4,779,624), Wollschlager in 1992 (Ultrasound endoscope device, U.S. Pat. No. 5,105,819), Sakamoto in 1994 (Ultrasound transmission medium feed device for endoscopically inserting ultrasound probe, U.S. Pat. No. 6,004,273) and recently in the patent application by Nierich in 2007 (Transmission device for ultrasonic imaging system, publication No. 2007/0038109). In all of these, there is balloon at the end of the endoscope encloses the transducer and is filled with water to permit acoustic coupling between the transducer and the luminal wall or other gastrointestinal structures. This is particularly helpful in the part of gastrointestinal tract where the diameter of the lumen is small and the inflated balloon makes a good circumferential contact with the intestinal wall and thus creates a good acoustic coupling. In most parts of the gastrointestinal tract, however, the large diameter of the lumen and or the angle of the transducer in relation to the intestinal wall result in an inadequate contact between the transducer balloon and the intestinal wall and thus, the operators usually use water infusion to fill the region of the gastrointestinal tract with water and create acoustic coupling between the transducer and the examined structures. Unfortunately, the gastrointestinal tract is not a closed region and the infused water soon moves to other regions of the gastrointestinal tract. This can often result in poor image quality despite repeated infusion of water around the transducer. In addition, infusion of significant amount of water during the examination could result in untoward problems such as aspiration of the water into the patient's airway or overdistention of the gastrointestinal tract. To overcome this problem I have devised a device that creates a closed space around the ultrasound transducer using two balloons. Using two balloons in the gastrointestinal system has been suggested for the first time by Wilcox in 1987 (Double balloon nasobiliary occlusion catheter for treating gallstones and method of using the same U.S. Pat. No. 4,696,668) who used a double balloon catheter to make a closed space inside the bile duct to direct the chemicals used for lysing of gall bladder stone into the gall bladder and limit the exposure of the rest of the biliary system with this toxic agent. Later a two balloon approach was used on various endoscopic devices for assisting the movement of the endoscope deep down into the small intestine. The initial devices was proposed by Fujikura in 2005 (Insertion assisting tool for endoscope, publication No. 2005/0124856), Takano in 2005 (Endoscope apparatus, publication No. 2005/0165273), Machida in 2005 (Endoscope apparatus, publication No. 2005/0215855), and Yoshida in 2007 (Double-balloon endoscope system, publication No. 2007/0049797). In all these patents an overtube with a balloon is used to secure the position of the endoscope inside the gastrointestinal tract and the second balloon on the inserting tip of the endoscope is used to anchor and move the endoscope forward using alternating inflating and deflating of these two balloons.

Another device was described in U.S. Publication No. 2005/0107664 to Kalloo et al. which proposes an elongated dilating balloon serves to provide a uniform dilation of the stomach wall and two inflatable balloons affixed to the distal end of the overtube. Inflation of these two balloons can create a seal around the overtube while the overtube passes through a body cavity. The seal created by these two balloons can act like a barrier between two body cavities in his case between stomach and intra-abdominal cavity (peritoneum). In contrast to Kalloo's design, where two balloons are located at the distal end of the overtube, in the claimed device an inflatable positioning ring is affixed to the overtube at the distal end and an occlusion balloon is affixed a catheter at the distal end. The catheter passes through a passageway defined by the overtube. In Kalloo's device the balloons function to create a seal between two cavities (gastrointestinal lumen and peritoneal cavity). The present device however creates a sealed region in a single cavity (the gastrointestinal lumen). In Kalloo's device both balloons are in fixed position, but in the claimed design the positioning of the sealing devices is independent of one another. Also an elongated dilating balloon can be used to help to pass the overtube through a cut that is made in the gastrointestinal lumen. This dilating balloon passes through a passageway that is located within the endoscope and differs from the claimed occlusion balloon at the end of a catheter that passes through a passageway defined by the overtube. This gives this occlusion balloon freedom to move independently of the endoscope. In fact, there is no need to have an endoscope to deploy the occlusion balloon. The dilating balloon in Kalloo's device can only be introduced if the endoscope has already placed inside the overtube. In addition, in Kalloo's design, dilation balloon is just an accessory that is needed to temporarily dilate the opening of the incision in the stomach to help the passage of the overtube through the opening.

Another device was proposed application 20090227835 by Terliuc. This device is a flexible small overtube that is assembled on the distal shaft of an endoscope and then travels with the endoscope inside the body cavity. This overtube is fixed over the shaft of the endoscope and cannot be placed or moved independent of the endoscope in oppose to my invention which allows the endoscope to move freely and independently inside of the overtube. In fact, the endoscope can even be replaced with another endoscope while the overtube can be kept in its position. In addition, the overtube cannot be moved independent of the endoscope inside the body cavity since the proximal end of the said overtube is also inside of the body cavity while my claimed invention has a proximal end that is situated outside of the body cavity and can be moved independent of endoscope.

Another device is shown in Wenner et al. U.S. Pat. No. 6,440,061. Wenner et al. proposed an overtube with a catheter situated within a catheter tube and a free, independently positionable distal endportion that terminates in an inflatable occlusion balloon that exits from the side of the flexible overtube but not the end of the flexible overtube. Thus, it cannot create a liquid tight space at the end of the overtube. This is because the occlusion balloon in Wenner's patent is situated at the same side as the positioning balloon in relation to the end of the endoscope. In contrast, the present claims define an occlusion balloon and a positioning ring independently positioned on the proximal and the distal positions in relation to the end of the endoscope, thereby, creating a liquid tight space around the end of the endoscope. In fact, if the occlusion balloon of the Wenner's invention was to exit from the end of the flexible overtube and placed distal to the end of the endoscope the purpose of their invention, access of endoscope to the site of interest would be prevented since the endoscope view and access would have been blocked by the occlusion balloon. In addition, passage of a flexible tube into body cavity needs a rigid introducer sheath while in the current invention the overtube is being inserted into the body cavity over the endoscope and uses endoscope as the guide. The overtube also has a curved lower distal end and an angled tip, which is designed to work in an acute angled spot such as bile duct. This prevents this device to work similar to my device, which has a straight distal end in the gastrointestinal (GI) tract. And last but not least, there is no structure in overtube that can create a hydraulic seal between the endoscope and overtube. Thus, fluid can leak around the endoscope since device cannot create nor maintain a hydraulic sealed area distal to the tip of the overtube between the positioning balloon and the occlusion balloon similar to the current invention. Wenner's device can uses two occlusion balloons called first and second occlusion balloon that both can pass through overtube sheath ports to create a hydraulically sealed area between these two balloons but the hydraulically isolated region is not between an occlusion balloon and a positioning ring at the distal of the overtube. Not to mention that the device is not designed and cannot achieve hydraulically sealed region due to lack of any structure in the overtube to seal the endoscope within the overtube.

Yet another device was proposed by Chu et al. U.S. Pat. No. 5,916,145. In this device a flexible mesh overtube is inserted with the use of endoscope shaft as a guide and a distal housing that includes a suction chamber and an endoscope chamber on its distal end. Between the endoscope chamber and the suction chamber, there is a clear window which allows the endoscopic view of the area distal to the overtube through this window. The endoscope tip does not exit the distal end of overtube. This allows the endoscope to stay away from contaminants per inventors' point of view. The only access to the body cavity is through a passageway which allows using tools such as forceps or catheters distal to the tip of the overtube. A fundamental difference between this device and the current invention is that the endoscope exits the distal end of the overtube into body cavity in the current invention. In fact, for devices such as echoendoscope, it is essential for the distal tip of endoscope to touch the lining of the body cavity. In fact, the Chu overtube is not a through passageway for endoscope, and the entire mesh like mechanism works when the endoscope at the end pulls the distal end inside the body cavity by pushing force over its shaft. In addition, Chu et al. device does not have a catheter that terminates in an inflatable occlusion balloon as an integral part of the described overtube. There is mention of a possibility of using a dilation catheter that can be positioned in the distal end. The Chu et al. device fails to teach a structure that creates a seal inside the overtube and around endoscope since the distal end of endoscope at most abuts clear window or if there is no clear window, the tip of the endoscope cannot go beyond the overtube.

In the current invention, on the other hand the structure of the balloons and their functions are different.

SUMMARY OF THE INVENTION

The endoscope accessory embodying this invention enhances capabilities of an endoscope in maintaining luminal view and is comprised of an overtube having an inflatable, positioning ring at the distal endportion and which carries a catheter terminating in an occlusion balloon and also an internal sealing collar. Optionally, the overtube can be opened along its entire length, envelop the endoscope prior to insertion, and then slide over the endoscope inside the body cavity. Distal tip of the overtube is placed just proximal to the distal tip of the endoscope, and proximal to the region of the gastrointestinal tract that needs to be examined. The positioning ring is then inflated to secure the position of the overtube.

A catheter with an occlusion balloon at its distal endportion is carried by the overtube in a separate passageway or lumen in the overtube. The catheter extends beyond the tip of the endoscope distal to the region of the gastrointestinal tract that needs to be examined. Inflation of the occlusion balloon creates a closed space between the positioning ring and the occlusion balloon in the region of the gastrointestinal tract that needs to be examined. This closed space can be expanded with air, if desired, for detailed examination and treatment of the area with a regular endoscope, or filled with water for acoustic coupling between the endoscope transducer and gastrointestinal structures for examination with an echoendoscope.

The inflated balloons prevent escape of air or water from the examination site. This improves the acoustic coupling and provides for better examination in a relatively larger region of the gastrointestinal tract that needs to be examined. This reduces unnecessary overinflation of the other regions of the gastrointestinal tract with air and water, and in the case of water, reduces the risks such as aspiration. Throughout the procedure, the pressure within the positioning ring, occlusion balloon and the closed space between these two balloons can be monitored to prevent too much pressure at the area of the contacts of the balloons and gastrointestinal lining and also overdistension of the region between the two balloons with water or air. After termination of the examination, the overtube as well as endoscope can be removed after evacuation of the water or air from the closed space between the balloons as well as within the balloons.

In a preferred embodiment, an endoscope accessory embodying the present invention includes a flexible overtube with a reclosable longitudinal seam and an internal sealing collar, an inflatable positioning ring at the distal end of the overtube, a suction port proximal to and upstream of the positioning ring, a catheter lumen in the overtube, and a catheter terminating in an inflatable occlusion balloon. A suction passageway is also situated within the catheter and terminates in a suction tip that extends downstream of the occlusion balloon. The overtube seam can be opened along its entire longitudinal length and comprises an interlocking closure with cooperating coupling structures. The inflatable positioning ring is affixed to the overtube at the distal endportion thereof. Fluid conduits define a passageway for inflating or suctioning fluid and air within the gastrointestinal tract region subject to examination. A catheter is carried by the overtube and the midportion of the catheter passes through the wall of the overtube and the distal endportion of the catheter carrying the inflatable occlusion balloon is freely positionable within the gastrointestinal tract at a predetermined location. The catheter is a dual lumen catheter defining an inflation passageway for the occlusion balloon and a suction passageway that terminates in a suction tip downstream of the occlusion balloon that facilitates removal of secretions in the gastrointestinal tract downstream of the occlusion balloon.

BRIEF DESCRIPTION

DETAILED DESCRIPTION OF THE INVENTION

Figure 1:
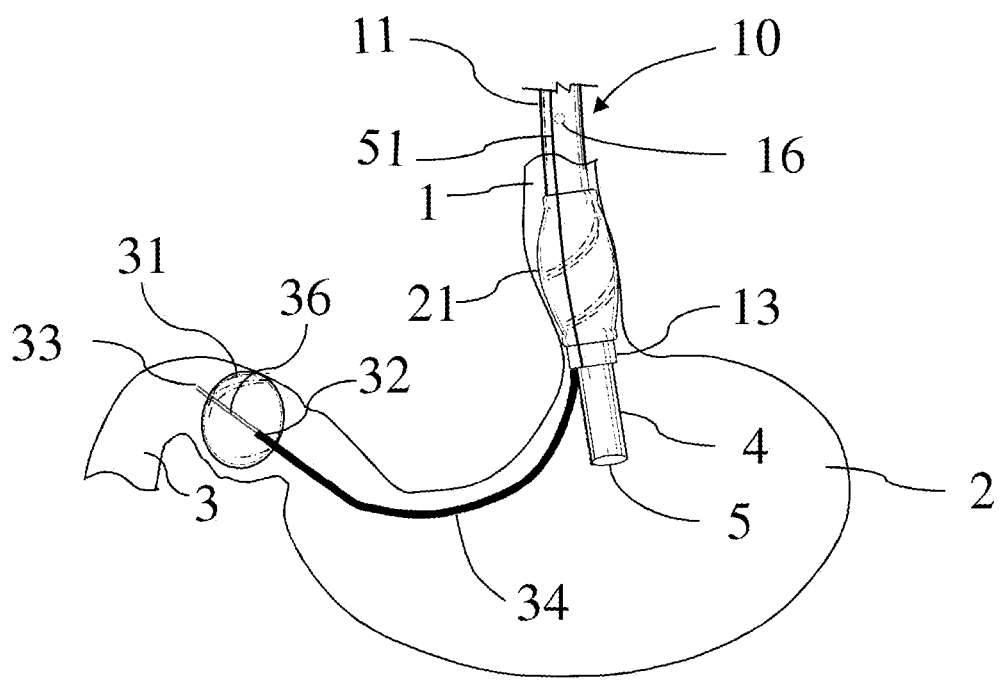
FIG. 1 is a schematic representation showing positioning of the endoscope accessory in use.
Figure 2:
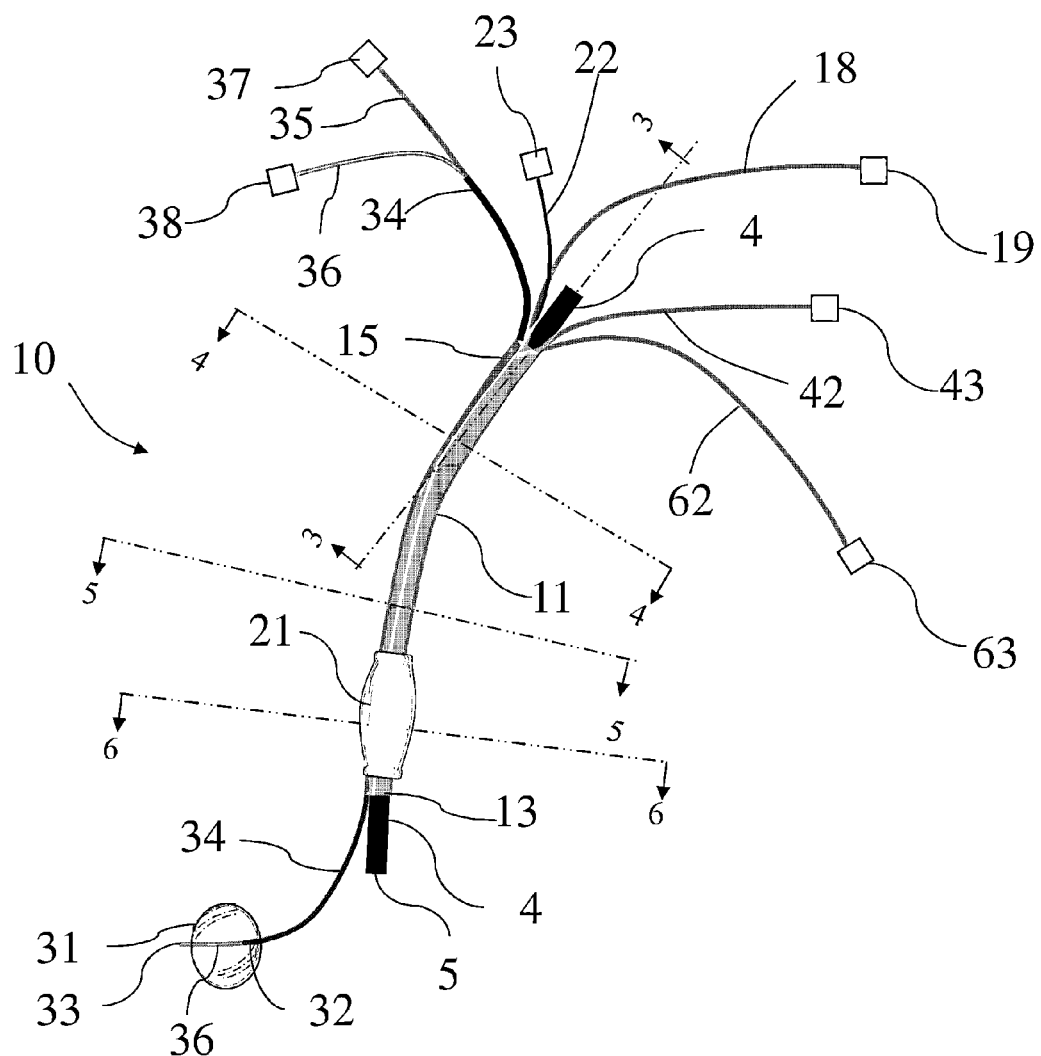
FIG. 2 is an overall plan view of the present invention.
Figure 3:
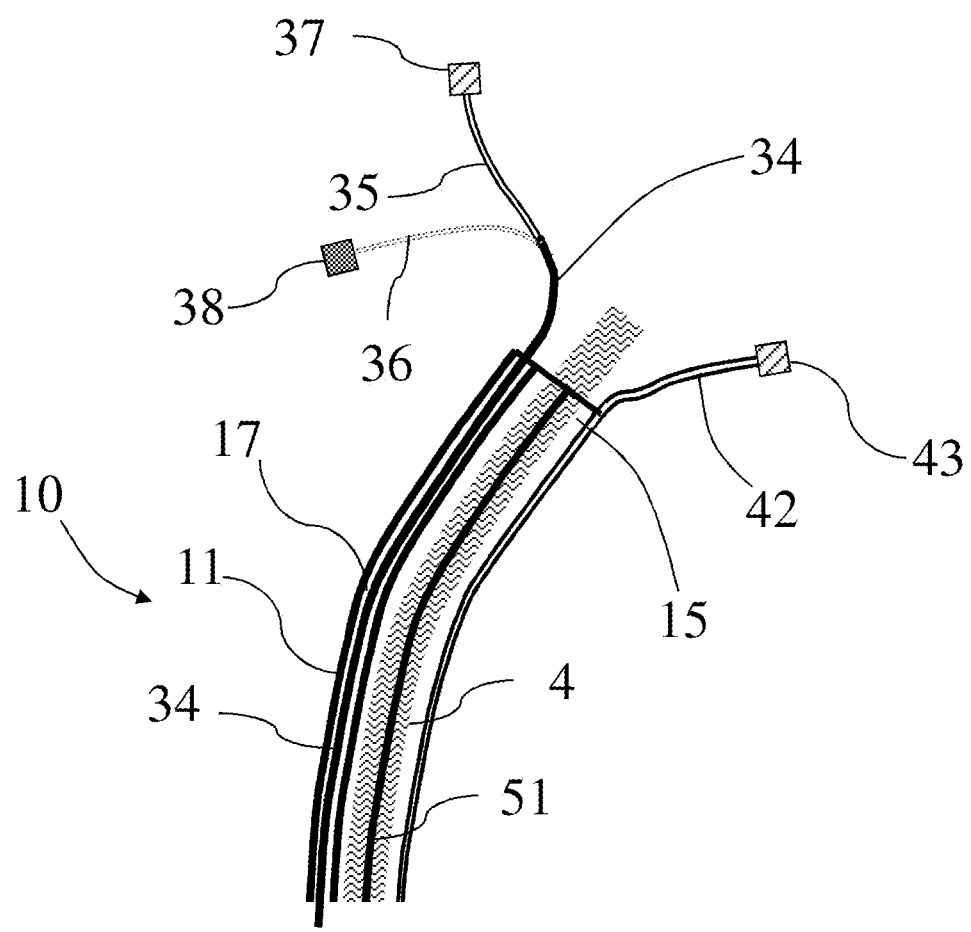
FIG. 3 is a longitudinal sectional view of the device shown in FIG. 2 taken along plane 3-3.

Endoscope Accessory 10 is made up of these components:

A—Overtube: As it is depicted in FIGS. 1 and 2, the endoscope accessory 10 is composed of a flexible overtube 11 that can be removably placed over a regular endoscope or echoendoscope shaft 4 and inserted inside a human body cavity such as gastrointestinal tract. The overtube has a proximal endportion 15 and a distal endportion 13. The endoscope tip 5 extends beyond the overtube distal endportion 13 within the body cavity (FIG. 1) for detailed examination of the body cavity. The overtube 11 has an optional longitudinal seam 51 along its entire length that allows opening of the overtube 11 along its entire length for placing an endoscope shaft 4 within the overtube 11 without the need for passing the endoscope through the overtube proximal endportion 15. Longitudinal seam 51 (FIGS. 1 & 7) can reversibly open and close using an interlocking closure mechanism at opposed adjacent edge portions 12 and 14. The interlocking closure mechanism can comprise cooperating coupling structures 52 and 53 (FIG. 8) and allows a reversible opening and closing of the longitudinal seam 51 along the entire length of the overtube 11. When the longitudinal seam 51 opens, the overtube can accept endoscope shaft 4 along its entire length and when it closes, it encloses the endoscope shaft 4 within the overtube 11, and defines a passageway for the endoscope. The endoscope can be any device used to access the body cavity such as conventional endoscope or echoendoscope. The overtube distal endportion 13 (FIGS. 1 & 2) is then inserted into the human body cavity over the endoscope shaft 4 that acts as a guide for placement of the overtube 11 inside the body cavity. After placement of the overtube 11 over the endoscope at the desired spot within the body cavity, an inflatable positioning ring 21 is inflated inside the body cavity to secure the position of the overtube inside the body cavity. When inflated, positioning ring 21 creates transient partitioning of the body cavity into two regions, Region 1 and Region 2. One proximal to the positioning ring 21 (Region 1) and another one distal to the positioning ring 21 (Region 2). The length of the overtube 11 is long enough so that when the distal overtube endportion 13 is secured inside the body cavity, the overtube proximal endportion 15 (FIG. 2) stays out of the human body and allows grasping and manipulation of the overtube 11 for proper positioning of the overtube proximal endportion 13 inside the body cavity by the endoscopist. The diameter of the overtube 11 is wide enough to freely receive a regular endoscope or echoendoscope shaft 4 therewithin. The other features include:

An inflation tube 22 carried by the overtube 11 that distally connects to the positioning ring 21 and proximally extends beyond the overtube proximal endportion 15 and is used to inflate the positioning ring 21. There is a connection piece 23 at the proximal end of the inflation tube 22 that can be used to connect the inflation tube 22 to an inflating device for inflating and monitoring the pressure within the positioning ring 21.

Fluid conduit 42 is carried by the overtube 11 that has an opening at the distal overtube endportion 13 and proximally extends beyond the overtube proximal endportion 15 and is used to infuse or empty the water or air inside the body cavity Region 2 at the region of the gastrointestinal tract that needs to be examined There is a connection piece 43 at the proximal end of the fluid conduit 42 that can be used to connect to an inflating device for inflating and monitoring the pressure within the body cavity Region 2.

Catheter lumen 17 defined by the overtube 11 that has an opening at the distal overtube endportion 13 and an opening at the proximal endportion 15 and is used as a passageway for the receiving catheter 34 as well as an occlusion balloon at the distal endportion of the catheter.

Figure 5:
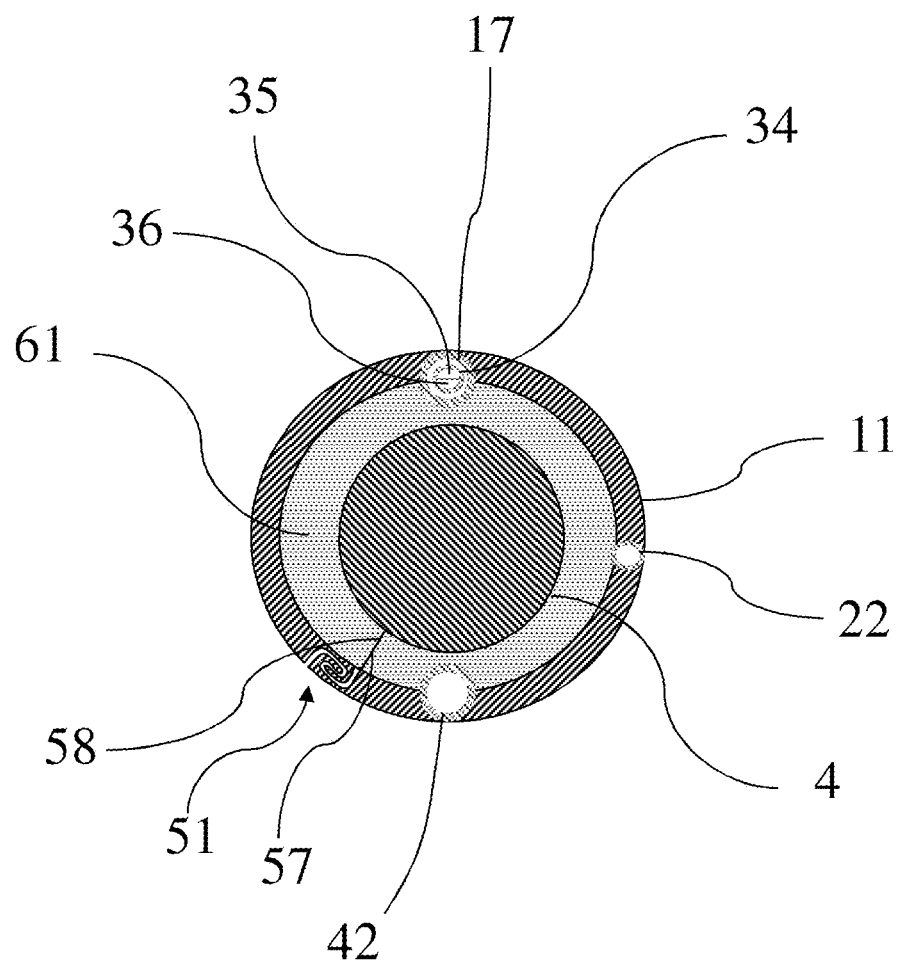
FIG. 5 is a sectional view of the device shown in FIG. 2 taken along plane 5-5.

A sealing collar 61 (FIG. 5) at the overtube midportion, usually upstream of balloon 21, is made of an inflatable tube which when inflated assumes a toroid-like configuration and creates a seal within the lumen of the overtube 11 between the shaft of the endoscope or echoendoscope 4 and the overtube 11, forms a fluid tight seal region at the overtube distal end 13 within the body cavity Region 2 and prevents leakage of air or water between the endoscope shaft 4 and overtube 11. When inflated, end faces 57 and 58 of collar 61 abuts. Collar 61 permits free sliding movement of the shaft of the endoscope or echoendoscope 4 within the lumen of the overtube 11 during the examination while maintaining the sealing function. When deflated, the endoscope could be easily removed from the overtube and or another endoscope be replaced within the overtube. In this situation, the overtube acts as a guide for the insertion of the new endoscope.

Figure 4:
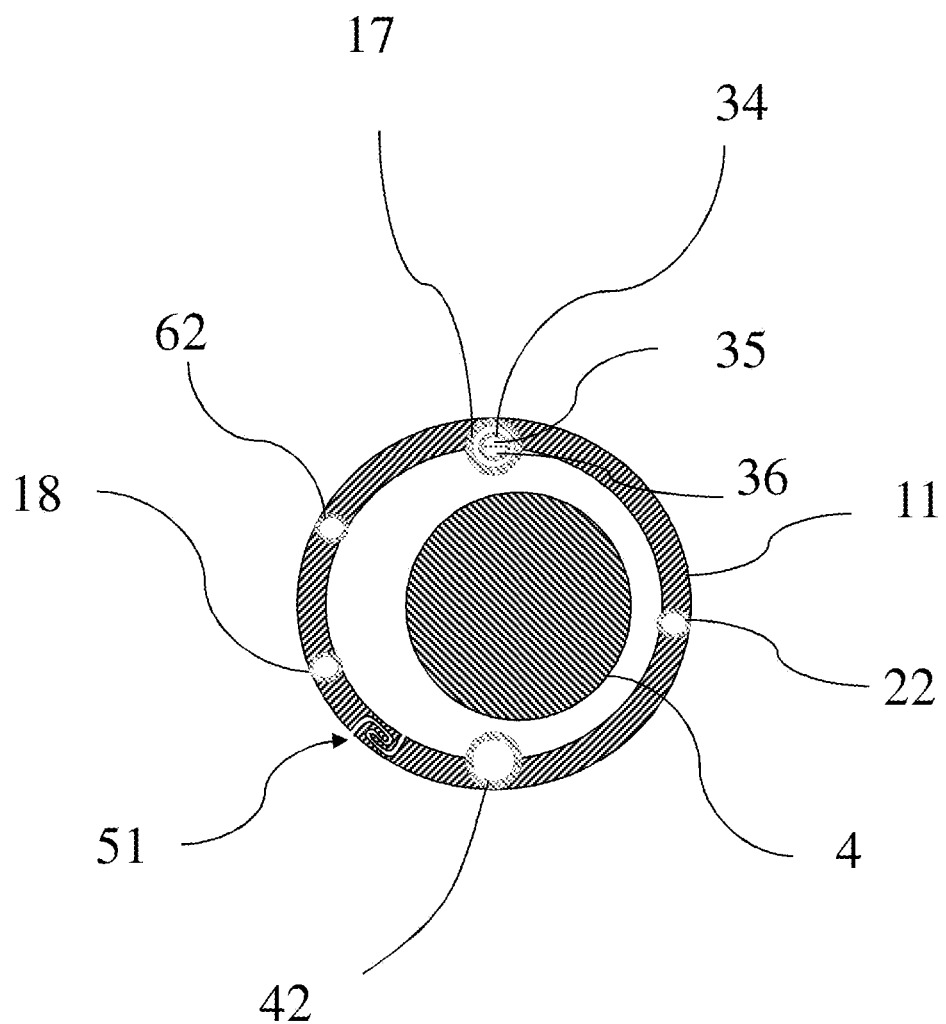
FIG. 4 is a sectional view of the device shown in FIG. 2 taken along plane 4-4.

A suction conduit 18 (FIGS. 2 & 4) is carried by the overtube 11 terminates in a suction port 16 (FIG. 1) at the midportion outside surface of the overtube 11 and proximally extends beyond the overtube proximal endportion 15. Suction conduit 18 is used for suctioning air and fluid accumulated proximal to the positioning ring 21 within the body cavity Region 1. A connection piece 19 at the proximal end of the suction conduit 18 that can be used to connect the conduit 18 to a suction device.

Figure 6:
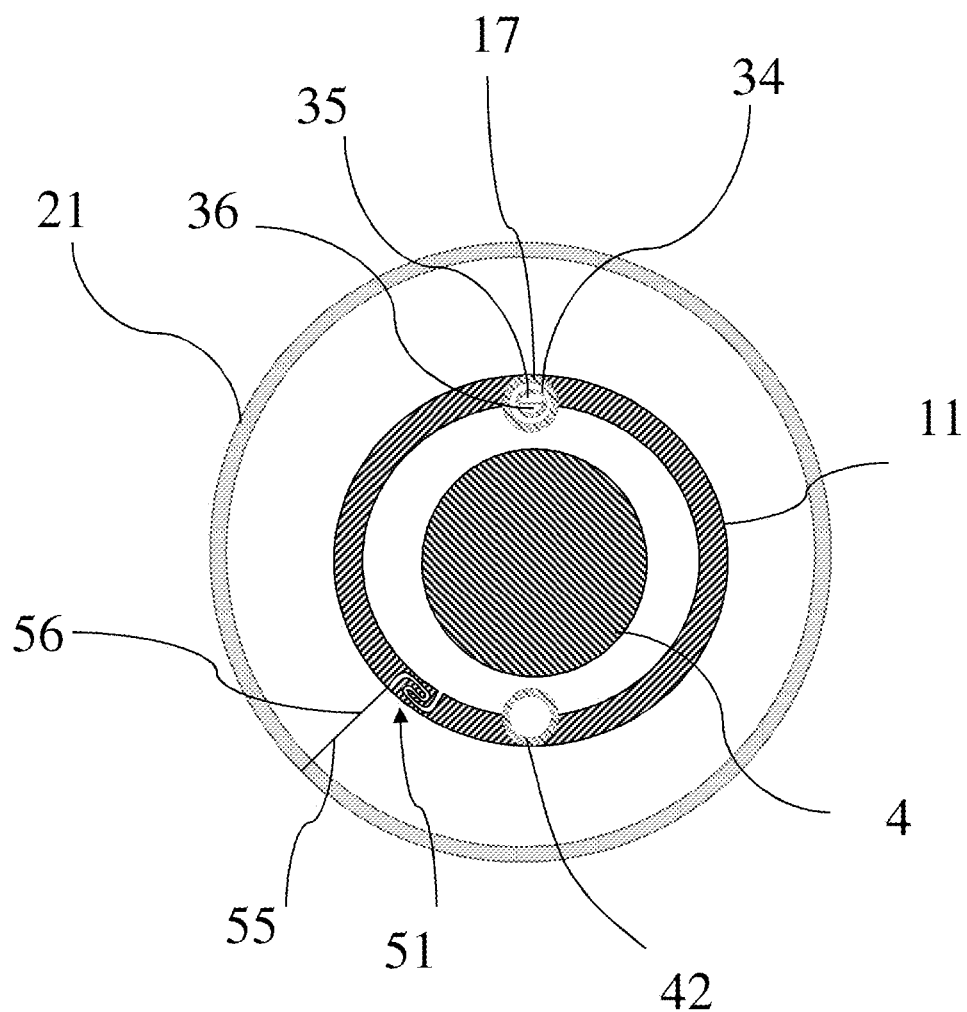
FIG. 6 is a sectional view of the device shown in FIG. 2 taken along plane 6-6.
Figure 7:
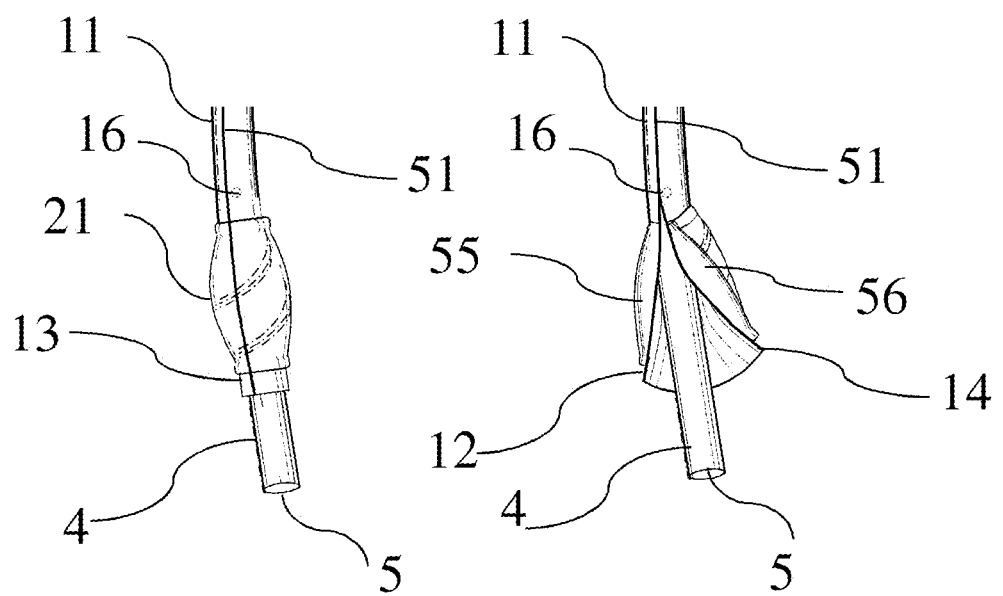
FIG. 7 is a partial view of the tip of the overtube and shows how longitudinal seam of the overtube can open from its distal end.
Figure 8:
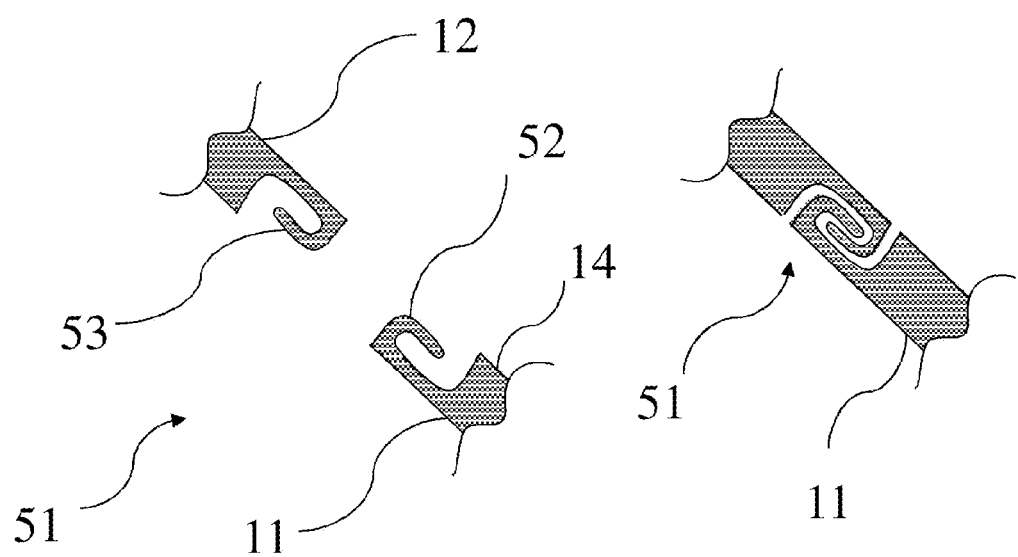
FIG. 8 is a partial sectional view of the longitudinal seam that can open and close along the entire length of the overtube in a zipper like action.

As shown in FIG. 7, overtube 11 can be provided with a reclosable longitudinal seam 51 which can be opened to receive endoscope shaft 4 and thereafter closed to envelop the endoscope shaft 4 by a zipper like closure, a hook and loop type closure, and the like. End faces 55 and 56 of positioning ring 21 abut when positioning ring is inflated (FIG. 6).

B—Catheter and Occlusion balloon: As it is depicted in FIGS. 1 and 2, the dual lumen catheter 34 defines two flexible passageways, inflation passageway 35 and suction passageway 36. Dual lumen catheter 34 has a distal free endportion 32 that can be independently positioned distal to the overtube 11 within the body cavity and has an inflatable occlusion balloon 31 affixed to its distal free endportion 32. When occlusion balloon 31 is inflated, it creates a transient partitioning of the body cavity further into 3 regions, Region 1, Region 2 and Region 3. One region 3 distal to the occlusion balloon 31 (Region 3), one region 2 proximal to occlusion balloon 31 and distal to the positioning ring 21 (Region 2) and another region 1 proximal to the positioning ring 21 (Region 1).

An inflation passageway 35 carried by the catheter 34 distally terminates at catheter 34 distal free endportion 32 and connects to the occlusion balloon 31 and proximally connects to a connection piece 37, and is used to inflate the occlusion balloon 31. The connection piece 37 at the proximal end of the inflation tube 35 can be used to connect the inflation tube 35 to an inflating device for inflating and monitoring the pressure within the occlusion balloon 31. Suction conduit 36.

Suction passageway 36 in catheter 34 passes through the occlusion balloon 31 and terminates in a suction tip 33 downstream of occlusion balloon 31. Suction passageway 36 proximally connects to a connection piece 38, and is used for suctioning air and fluid accumulated downstream of the occlusion balloon 31 within the body cavity Region 3. The connection piece 38 at the proximal end of the suction passageway 36 can be used to connect the suction passageway 36 to a suction device.

In use, after insertion of the endoscope or echoendoscope shaft 4 into the patient's body cavity, the overtube 11 is opened along its entire length using the longitudinal seam 51 and then enclosed over the shaft of the endoscope 4 using the longitudinal seam 51 zipper like closing mechanism. While the distal portion of the endoscope or echoendoscope is within the body cavity, the overtube 11 is slid over the endoscope or echoendoscope shaft 4 into the body cavity and advanced so that the overtube distal endportion 13 gets to the desired region of the body cavity just proximal to the endoscope tip 5. At this point the positioning ring 21 at the overtube distal endportion 13 is inflated to secure the position of the overtube 11 and create transient partitioning of the body cavity into two regions, Region 1 and Region 2. One proximal to the positioning ring 21 (Region 1) and another one distal to the positioning ring 21 (Region 2).

Then catheter 34 carrying affixed occlusion balloon 31 at its free endportion 32 is inserted into the catheter tube 17 and is advanced into the body cavity Region 2 distal to the tip of the endoscope 5. After placing the tip of catheter 34 at the desired spot, the occlusion balloon 31 is inflated to create a transient partitioning of the body cavity further into 3 regions, Region 1, Region 2 and Region 3. One distal to the occlusion balloon 31 (Region 3), one proximal to occlusion balloon 31 and distal to the positioning ring 21 (Region 2) and another one proximal to the positioning ring 21 (Region 1). The portion of the body cavity that needs to be examined is in Region 2.

The sealing collar 61 is then inflated to create a seal within the lumen of the overtube 11 between the shaft of the endoscope or echoendoscope 4 and the overtube 11. It is important to form a fluid tight seal area at the overtube distal end 13 within the body cavity Region 2 by preventing leakage of air or water between the endoscope shaft 4 and overtube 11. This creates a closed region in the body cavity Region 2 around the tip of endoscope or echoendoscope 5 that could be insufflated with air for examination with regular endoscope or with water for examination with echoendoscope. The water or air is introduced into or removed from this closed region using fluid conduit 42. The pressure inside the body cavity Region 2 is continuously measured, and can be adjusted by infusion or evacuation of the water or air through conduit 42.

Throughout the examination fluid and air accumulated upstream to the positioning ring 21 in the body cavity Region 1 is continuously suctioned out of the body cavity using suction port 16 and associated suction conduit 18. Fluid and air accumulated downstream of the occlusion balloon 31 in the body cavity Region 3 is continuously suctioned outside of the body cavity using suction tip 33 associated with suction passageway 36.

After completion of the examination, the air or water within the body cavity Region 2 is suctioned out via fluid conduit 42. After complete evacuation of air or water from body cavity Region 2, the positioning ring 21, occlusion balloon 31 and sealing collar blare all deflated, and the overtube 11 as well as endoscope can be removed independent of each other from the body cavity.

The forgoing description and the drawing are illustrative of the invention and are not to be taken as limiting. Still other variants and rearrangements of structural parts are possible without departing from the spirit and scope of this invention and will readily present themselves to those skilled in the art.

The invention claimed is:

1. An endoscope accessory which comprises:
   a flexible overtube having a distal endportion, a proximal endportion, and defining a central through passageway for receiving there within an endoscope or echoendoscope shaft and a catheter lumen in a wall portion of the overtube;
   a reclosable seam is provided along the length of the flexible overtube through which the endoscope or echoendoscope shaft is placed lengthwise within the flexible overtube;
   an inflatable positioning ring around the overtube at the distal end portion thereof, wherein the positioning ring includes two end faces internally oriented and lengthwise positioned adjacently to opposed adjacent edge portions of the reclosable seam, and wherein the two end faces abut when the positioning ring is inflated and the reclosable seam is closed, and are unabutted when the positioning ring is deflated and the reclosable seam is opened to place the endoscope or echoendoscope shaft lengthwise within the flexible overtube;

a ring inflation tube in fluid communication with the positioning ring;

an inflatable sealing collar within the overtube;

a collar inflation tube in fluid communication with the sealing collar; and a catheter situated within the catheter lumen and having a free, independently positionable distal endportion that terminates in an inflatable occlusion balloon, wherein an inflation of the occlusion balloon the positioning ring and the sealing collar creates a closed space within a body cavity that is fillable with air and water for improving an examination with the endoscope or the echoendoscope shaft.

2. The endoscope accessory in accordance with claim 1 wherein the reclosable seam is used for placing the endoscope or echoendoscope shaft within the overtube without a need for passing the endoscope or echoendoscope shaft through the proximal endportion.

3. The endoscope accessory in accordance with claim 2 wherein the sealing collar terminates in abutting faces when inflated.

4. The endoscope accessory in accordance with claim 1 wherein the overtube defines a suction port proximal to and upstream of the positioning ring and wherein a suction conduit in fluid communication with the suction port is carried by the overtube.

5. The endoscope accessory in accordance with claim 1 wherein the catheter is a dual lumen catheter defining an inflation passageway for the occlusion balloon and a suction passageway that terminates in a suction tip downstream of the occlusion balloon.

6. An endoscope accessory which comprises:

a flexible overtube having a distal endportion, a proximal endportion, and defining a central through passageway for receiving there within an endoscope or echoendoscope shaft and a catheter lumen in a wall portion of the overtube;

a reclosable seam is provided along the length of the flexible overtube through which the endoscope or echoendoscope shaft is placed lengthwise within the flexible overtube;

an inflatable positioning ring around the overtube at the distal end portion thereof, wherein the positioning ring includes two end faces internally oriented and lengthwise positioned adjacently to opposed adjacent edge portions of the reclosable seam, and wherein the two end faces abut when the positioning ring is inflated and the reclosable seam is closed, and are unabutted when the positioning ring is deflated and the reclosable seam is opened to place the endoscope or echoendoscope shaft lengthwise within the flexible overtube;

a ring inflation tube in fluid communication with the positioning ring;

an inflatable sealing collar within the overtube;

a collar inflation tube in fluid communication with the sealing collar;

a catheter situated within the catheter lumen and having a free, independently positionable distal endportion to which is affixed an inflatable occlusion balloon, wherein an inflation of the occlusion balloon the positioning ring and the sealing collar creates a closed space within a body cavity that is fillable with air and water for improving an examination with the endoscope or the echoendoscope shaft; and a suction passageway located internally in the catheter, which is a dual lumen catheter and includes internally an inflation passageway for the occlusion balloon, wherein the suction passageway passes through the occlusion balloon and terminates in a suction tip outside of the occlusion balloon within a second body cavity separated from the closed space by the inflated occlusion balloon, wherein the suction passageway is used for suctioning air and fluid accumulated within the second body cavity.

7. The endoscope accessory in accordance with claim 6, wherein the suction passageway is connected to a connection piece at a proximal end of the suction passageway.

8. The endoscope accessory in accordance with claim 7, wherein the connection piece is used to connect the suction passageway to a suction device.

9. The endoscope accessory in accordance with claim 6, wherein the reclosable seam is used for placing the endoscope or echoendoscope shaft within the overtube without a need for passing the endoscope or echoendoscope shaft through the proximal endportion.

10. The endoscope accessory in accordance with claim 9, wherein the sealing collar terminates in abutting faces when inflated.

11. The endoscope accessory in accordance with claim 6, wherein the overtube defines a suction port proximal to and upstream of the positioning ring and wherein a suction conduit in fluid communication with the suction port is carried by the overtube.

12. An endoscope accessory which comprises:

a flexible overtube having a distal endportion, a proximal endportion, and defining a central through passageway for receiving there within an endoscope or echoendoscope shaft and a catheter lumen in a wall portion of the overtube;

a reclosable seam is provided along the length of the flexible overtube through which the endoscope or echoendoscope shaft is placed lengthwise within the flexible overtube;

an inflatable positioning ring around the overtube at the distal end portion thereof, wherein the positioning ring includes two end faces internally oriented and lengthwise positioned adjacently to opposed adjacent edge portions of the reclosable seam, and wherein the two end faces abut when the positioning ring is inflated and the reclosable seam is closed, and are unabutted when the positioning ring is deflated and the reclosable seam is opened to place the endoscope or echoendoscope shaft lengthwise within the flexible overtube;

a ring inflation tube in fluid communication with the positioning ring;

an inflatable sealing collar within the overtube, which terminates in abutting faces when inflated;

a collar inflation tube in fluid communication with the sealing collar; and a catheter situated within the catheter lumen and having a free, independently positionable distal endportion that terminates in an inflatable occlusion balloon, wherein an inflation of the occlusion balloon, the positioning ring and the sealing collar creates a closed space within a body cavity that is fillable with air and water for improving an examination with the endoscope or the echoendoscope shaft.

13. The endoscope accessory in accordance with claim 12, wherein the reclosable seam is used for placing the endoscope or echoendoscope shaft within the overtube without a need for passing the endoscope or echoendoscope shaft through the proximal endportion.

14. The endoscope accessory in accordance with claim 12, wherein the flexible overtube defines a suction port proximal to and upstream of the positioning ring and wherein a suction conduit in fluid communication with the suction port is carried by the overtube.

15. The endoscope accessory in accordance with claim 12, wherein the catheter is a dual lumen catheter defining an inflation passageway for the occlusion balloon and a suction passageway that terminates in a suction tip downstream of the occlusion balloon.

* * * * *